United States Patent [19]

Terauchi

[11] 4,281,655
[45] Aug. 4, 1981

[54] AUTOMATIC URINE COLLECTING APPARATUS

[76] Inventor: Ryugo Terauchi, 4-29-18, Minamiogikubo, Suginami-ku, Tokyo-to, Japan

[21] Appl. No.: 79,012

[22] Filed: Sep. 26, 1979

[51] Int. Cl.³ ............................................. A61M 1/00
[52] U.S. Cl. ...................................... 128/278; 4/305
[58] Field of Search ............... 128/294, 295, 276, 278; 15/346, 345; 137/205; 4/305, 306, 144.1, 144.3, 144.4

[56] References Cited

U.S. PATENT DOCUMENTS

| | | | |
|---|---|---|---|
| 1,105,488 | 7/1914 | Clave | 128/295 |
| 2,626,385 | 1/1953 | Schumann | 128/295 UX |
| 2,840,079 | 1/1958 | Conway et al. | 128/295 |
| 2,944,551 | 7/1960 | Breer | 128/295 |
| 3,114,916 | 12/1963 | Hadley | 4/144.3 |
| 3,194,238 | 7/1965 | Breece, Jr. | 128/295 |
| 4,015,613 | 4/1977 | Papworth | 15/346 |
| 4,084,589 | 4/1978 | Kului | 128/295 |

FOREIGN PATENT DOCUMENTS

| | | | |
|---|---|---|---|
| 123134 | 1/1947 | Australia | 128/295 |
| 992462 | 10/1951 | France | 128/295 |
| 223258 | 8/1968 | U.S.S.R. | 128/295 |
| 304728 | 7/1971 | U.S.S.R. | 128/295 |

Primary Examiner—Stephen C. Pellegrino
Assistant Examiner—J. L. Kruter
Attorney, Agent, or Firm—Cullen, Sloman, Cantor, Grauer, Scott & Rutherford

[57] ABSTRACT

When an elderly person is confined to bed, or a patient is suffering from a spinal cord injury, and has the automatic urine collecting apparatus of this invention fastened to him, has urine incontinence, the sensor of the system detects the first drop of discharged urine. The urine is automatically carried along with the air sucked from the urine receiving unit and transmitted to a urinal. The air is supplied to the urine receiving unit through a multitude of small holes bored at the top thereof and a soft vinyl tube connected thereto and extended outside. To further supply air into the urine receiving unit, said vinyl tube may be connected to a pipe discharging the exhaust air during the time a pump is operating. A warm water feed pipe may be connected to said vinyl tube for cleansing the patient's private parts.

2 Claims, 2 Drawing Figures

AUTOMATIC URINE COLLECTING APPARATUS

Hitherto, when a patient suffering from urine incontinence, i.e., a patient suffering from spinal cord injury, and an elderly person confined to bed or in decrepitude, has urine incontinence in bed, diapers have to be replaced by an attendant several times a day, causing many difficulties in the washing, drying, and disposal of the diapers.

In urine collecting methods used hitherto, a bag made of rubber, polyethylene, or vinyl chloride is attached to patient's private parts, and it must be replaced at intervals by an attendant. In all of these methods, the patient's skin at the affected part tends to become sore due to moisture, causing the patient to suffer from inconvenience and discomfort.

An object of this invention is to collect urine excreted into a urine receiving unit by aerial suction into a urinal.

Another object of this invention is to speed up the discharge of urine and to prevent patient's skin from becoming sore due to moisture.

A further object of this invention is to cleanse the patient's private parts by pouring warm water into the urine receiving unit.

A still further object of this invention is to secure the urine receiving unit by use of a rubber ring, without causing injury to the patient's skin.

This invention is intended to achieve the aforementioned objectives, and is concerned with an automatic urine collecting apparatus comprising; fitting an annular rubber tube, which is kept in contact with the patient's skin, at an end of a urine receiving unit, putting said annular rubber tube through a hole in a fitting cloth, boring a multitude of small holes and installing a soft airtube at the outer top of said urine receiving unit, connecting the opposite end of said urine receiving unit to a urinal via a sensor and a urine sucking vinyl tube, connecting urinal to a suction pump in an electric power unit by a vinyl tube, and connecting said sensor to the electric power unit by an electric wire.

Figure 1:
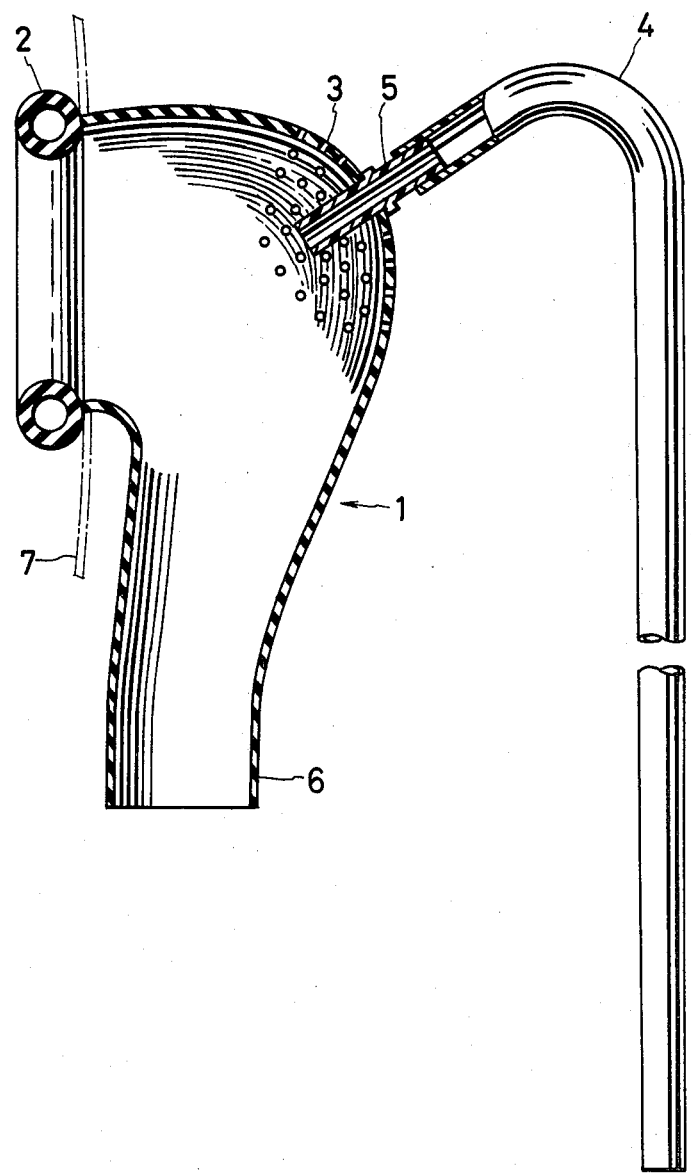
FIG. 1 is a longitudinal sectional view of the urine receiving unit.
Figure 2:
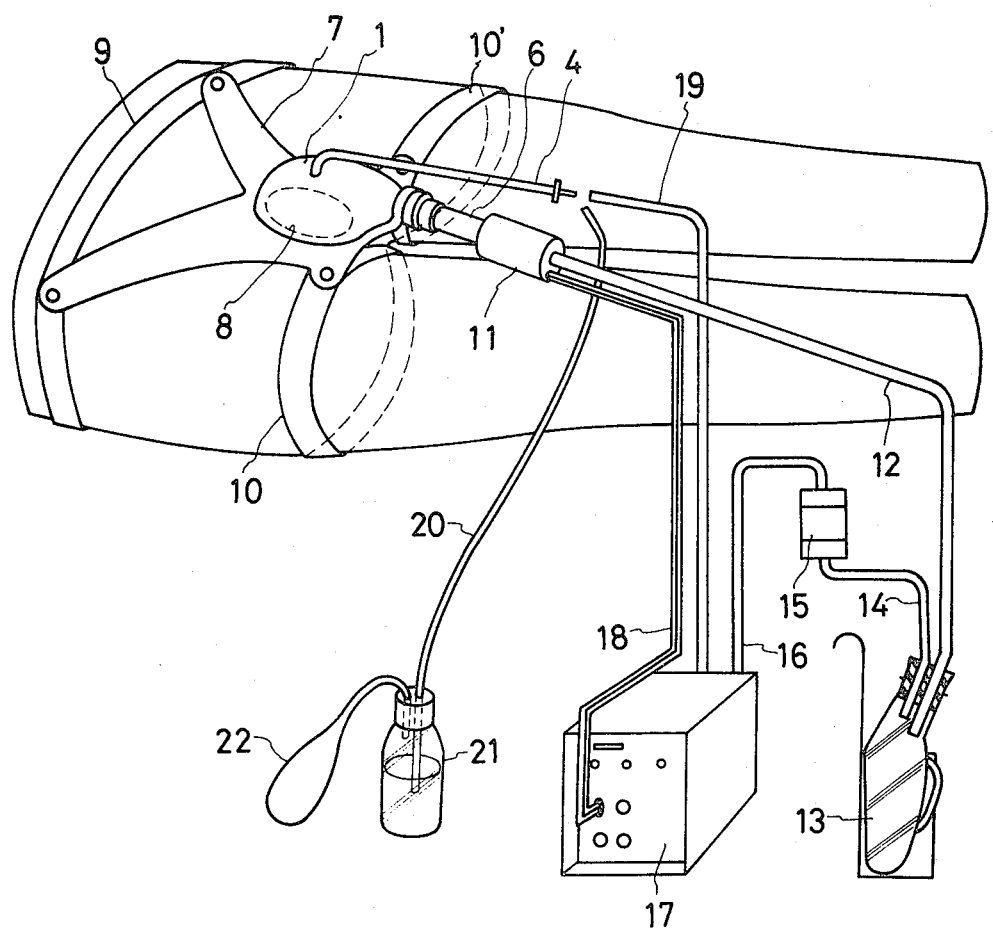
FIG. 2 is a perspective view showing the system in an operating condition.

An exemplary embodiment of this invention can be explained by the accompanying drawings.

The urine receiving unit is made of rubber curved at approximately a right angle, the top portion having a larger radius of curvature and the lower portion a smaller radius. An annular rubber tube 2 is attached to an end of said receiving unit 1. A plurality of small holes 3 are bored at the outer top of the unit. A soft vinyl tube 4 is connected thereto by the nozzle 5.

Said urine receiving unit extends through a hole of a fitting cloth 7, and is secured thereto by said annular rubber tube. The upper end of said fitting cloth is fastened to a strap 9, which is fastened around patient's waist. Annular rubber tube 2 of receiving unit 1 is kept in contact with the patient's skin and the patient's private parts are inserted into the urine receiving unit. Two straps 10 and 10' fastened to the lower end of the fitting cloth are fastened to each of the patient's thighs.

The lower end 6 of urine receiving unit 1 is connected to sensor 11 and the sensor 11 is connected by the urine suction vinyl tube 12 to urinal 13, which in turn is connected to an electric power unit 17 by way of vinyl tube 14, filter 15, and vinyl tube 16.

When urine is excreted, it is sensed by sensor 11 and the signal is transmitted to electric power unit 17 by electric wire 18 and the urine is sucked out by a suction pump in the power unit 17 and fed into urinal 13 through urine suction vinyl tube 12 from the urine receiving unit. The air in urinal 13 is filtered and any odor and moisture absorbed by filter 15 and is then circulated back the receiving unit through tubes 16 and 19.

When the outer surface of urine receiving unit is covered with diapers and vinyl cover which are to close the small holes of the top of the urine receiving unit, the exhausted air from the suction pump is to be supplied through vinyl tube 4, and the urine discharge is to be carried instantly to the urinal with the air circulation caused by the suction pump.

For that purpose, vinyl pipe 4 is to be connected with outlet of the air pipe 19.

Still further, when vinyl tube 4 is connected to hot water feed pipe 20 with the opposite end of the pipe inserted into bottle 21 filled with warm water and rubber bulb 22 is pressed, warm water can be fed into the curved pipe receiving unit 1 for cleansing the patient's private parts.

Vinyl tube 4 may be replaced manually with airpipe 19 or warm water feed pipe 20, as required.

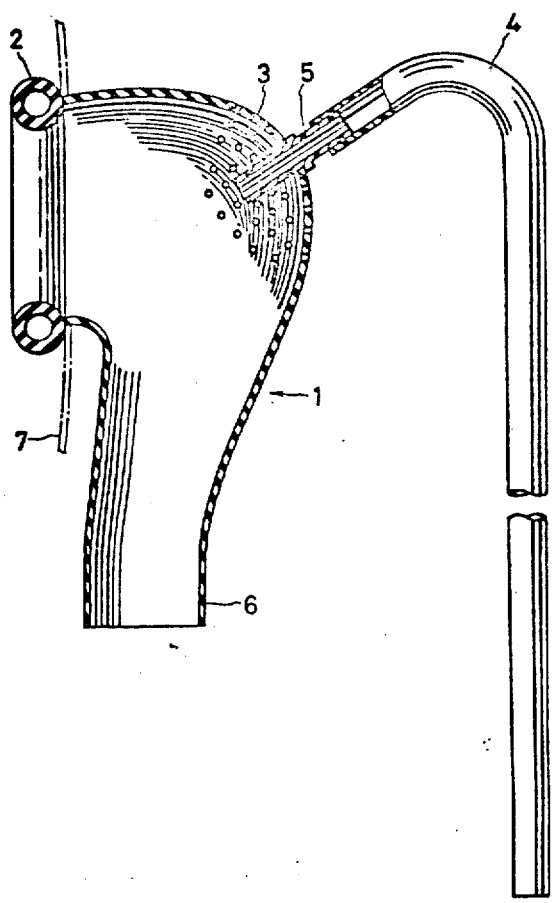

What is claimed is:

1. An automatic urine collecting apparatus comprising a tubular urine receiving unit having an inlet at its upper end and an outlet at its lower end;

an annular rubber tube connected to said inlet for contacting a patient's skin;

an apertured fitting cloth receiving said unit and retainingly engaging said rubber tube;

said urine receiving unit having at its intermediate outer top a plurality of apertures through which air enters;

a first flexible tube at one end connected to said unit adjacent said apertures;

an electronic sensor connected to the outlet of said unit for alternatively sensing the existence and non-existence of urine respectively;

a urinal having an upper end; a urine suctioning second plastic tube connecting said sensor to said urinal;

an electric power unit including a suction pump having an intake and an air pressure outlet;

a third plastic tube interconnecting said pump intake with said urinal at its upper end above the level of any liquid therein;

said sensor being electrically connected to said power unit to energize and deenergize said pump in response respectively to the existence and nonexistence of urine in said urine receiving unit;

a bottle filled with warm water; a warm water feeding pipe at one end projected into said bottle and at its other end adapted for connection to the other end of said first plastic tube;

and a rubber bulb connected to said bottle for applying air pressure into said bottle for selectively directing warm water through said feeding pipe into said urine receiving unit.

2. In the automatic urine collecting apparatus of claim 1, a flexible air pipe at one end removably connected to the other end of said first plastic tube and at its other end connected to said suction pump air pressure outlet adapted to feed air into said urine receiving unit.

* * * * *

UNITED STATES PATENT AND TRADEMARK OFFICE
CERTIFICATE OF CORRECTION

PATENT NO. : 4,281,655

DATED : August 4, 1981

INVENTOR(S) : Ryugo Terauchi

It is certified that error appears in the above—identified patent and that said Letters Patent is hereby corrected as shown below:

In the drawings delete Figure 1 and substitute the attached Figure therefore.

Signed and Sealed this

Third Day of November 1981

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,281,655

DATED : August 4, 1981

INVENTOR(S) : Ryugo Terauchi

It is certified that error appears in the above—identified patent and that said Letters Patent is hereby corrected as shown below:

FIG. 1